United States Patent
Kobayashi et al.

(10) Patent No.: US 7,189,379 B2
(45) Date of Patent: Mar. 13, 2007

(54) APPARATUS FOR METHANOL SYNTHESIS

(75) Inventors: Kazuto Kobayashi, Hiroshima (JP); Hiroyuki Osora, Hiroshima (JP); Hideaki Nagai, Tokyo (JP); Hiroshi Ohira, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/898,564

(22) Filed: Jul. 3, 2001

(65) Prior Publication Data
US 2002/0006972 A1 Jan. 17, 2002

Related U.S. Application Data

(62) Division of application No. 09/410,871, filed on Oct. 1, 1999, now Pat. No. 6,300,380.

(30) Foreign Application Priority Data
Oct. 2, 1998 (JP) .............................. 1998/280641

(51) Int. Cl.
*B01J 8/06* (2006.01)
*B01J 8/00* (2006.01)
*B01J 8/02* (2006.01)

(52) U.S. Cl. ...................... 422/196; 422/188; 422/193; 422/196; 422/197

(58) Field of Classification Search ................ 422/188, 422/189, 193, 196, 197, 187
See application file for complete search history.

(56) References Cited

U.S. PATENT DOCUMENTS 1,660,511 A * 2/1928 Jaeger .................. 422/109
1,945,353 A * 1/1934 Jaeger .................. 422/190
4,938,930 A * 7/1990 Shinkawa et al. .......... 422/148

* cited by examiner

*Primary Examiner*—Alexa D. Neckel
(74) *Attorney, Agent, or Firm*—Anderson Kill & Olick, P.C.

(57) ABSTRACT

An object of the present invention is to provide a production process for methanol in which a distillation system is reduced in a size by removing efficiently heat generated in a methanol synthesis reaction and inhibiting by-products from being formed. The present invention provides a production process for methanol comprising a synthetic gas production step in which hydrocarbon is reacted with steam to generate synthetic gas comprising main components of hydrogen, carbon monoxide and carbon dioxide, a methanol synthesis step in which the synthetic gas described above is reacted on a methanol synthesis catalyst and resulting crude methanol is recovered in the form of liquid and a distillation step in which recovered crude methanol described above is distilled to be separated into waste water containing low boiling organic compounds and high boiling organic compounds and refined methanol, wherein a reactor having a specific structure is used in the methanol synthesis step described above.

2 Claims, 4 Drawing Sheets

APPARATUS FOR METHANOL SYNTHESIS

This application is a divisional of Ser. No. 09/410,871, and claims priority to, U.S. Pat. No. 6,300,380 filed Oct. 1, 1999.

FIELD OF THE INVENTION

The present invention relates to a production process for methanol, more specifically to a production process for methanol in which a reactor having a structure capable of efficiently removing generated heat is used in a methanol synthesis step in producing methanol to inhibit by-products from being formed, whereby a compact distillation step (distillation system) is achieved.

DESCRIPTION OF RELATED ART

As shown, for example, in Japanese Patent Application Laid-Open No. 1-180841, a conventional process for producing methanol ($CH_3OH$) from hydrocarbon comprises usually the following steps (1) to (3). That is, they are:

(1) a synthetic gas production step in which gaseous hydrocarbon or vaporized liquid hydrocarbon reacts with steam in a reforming furnace at 800 to 1000° C. in the presence of a nickel base catalyst to produce synthetic gas comprising main components of hydrogen ($H_2$), carbon monoxide (CO) and carbon dioxide ($CO_2$);

(2) a synthesis step in which the synthetic gas described above reacts on a copper base methanol synthesis catalyst at a pressure of 50 to 150 atm and a temperature of 200 to 300° C. and resulting crude methanol is recovered from the reaction gas in the form of liquid; and (3) a distillation step in which liquid crude methanol is distilled in a distillation column comprising a single column or two or more columns to separate refined methanol from waste water containing organic compounds having lower boiling points than that of methanol (hereinafter referred to as low boiling organic compounds), organic acids and organic compounds having higher boiling points than that of methanol (hereinafter referred to as high boiling organic compounds).

In the synthesis step (2) described above, methanol ($CH_3OH$) is produced from carbon monoxide (CO) contained in the synthetic gas, and methanol ($CH_3OH$) and water ($H_2O$) are produced from carbon dioxide ($CO_2$). Impurities such as dimethyl ether, ethanol and the like are formed by side reaction in this synthesis step.

These impurities and water are contained in liquid crude methanol together with intended methanol but separated from methanol in the subsequent distillation step (3). In this case, there used to be involved the problem that if a lot of the impurities are contained, facilities for separation and refining in the distillation step are complicated and expanded in a size.

Various reactors having means and structures for controlling an increase in a gas temperature caused by an exothermic reaction during operation when carrying out synthesis by an exothermic reaction in the presence of a solid catalyst are devised for the reactor used in the synthetic step (2) described above. In this case, there has been the problem that as apparent from an effect of a temperature against a methanol equilibrium concentration, an increase in the temperature is accompanied with a reduction in the methanol equilibrium concentration in a methanol synthesis reaction to damage the profitability of the industrial plant.

On the other hand, even if a catalyst is used, the reaction rate is limited and reduced as the temperature is lowered, and therefore operation is desirably carried out in a proper temperature range from an industrial point of view considering the catalyst performance. For example, when methanol is synthesized from mixed gas comprising significant substances of hydrogen, carbon monoxide and carbon dioxide using a copper base catalyst, a temperature of 220 to 280° C. is considered to be appropriate. Further, a pressure of 50 to 300 $kg/cm^2 \cdot G$ is considered to be an economically proper pressure range for the pressure (total pressure) of gas. However, they are variable depending on an improvement in the catalyst.

OBJECT AND SUMMARY OF THE INVENTION

In light of the problems described above, the present inventors have made intensive investigations in order to develop a production process for methanol which can efficiently remove heat generated in a methanol synthesis reaction and which makes it possible to reduce the size of the distillation step (distillation system) by inhibiting by-products from being formed.

As a result thereof, the present inventors have found that such problems can be solved by using a reactor having a specific structure in a methanol synthesis step in producing methanol, in which an inner tube and a central tube are disposed in a reaction tube in the reactor and a granular catalyst is charged into a circular space surrounded by the reaction tube and the inner tube and in which the above central tube is disposed almost in the center of a shielding plate provided at the upper end of the reaction tube. The present invention has been completed from such point of view.

That is, the present invention provides a production process for methanol comprising a synthetic gas production step in which hydrocarbon reacts with steam to generate synthetic gas comprising main components of hydrogen, carbon monoxide and carbon dioxide, a methanol synthesis step in which the synthetic gas described above reacts on a methanol synthesis catalyst and resulting crude methanol is recovered in the form of liquid, and a distillation step in which recovered crude methanol described above is distilled to be separated into waste water containing low boiling organic compounds and high boiling organic compounds and refined methanol, wherein used in the methanol synthesis step described above is a reactor which comprises a reaction tube, an inner tube closed at a lower end thereof disposed almost in the center of the reaction tube, a central tube in which unreacted feed gas flows disposed almost in the center of the above inner tube, and a circular catalyst layer charged with a granular catalyst disposed in a circular space surrounded by the reaction tube and the inner tube and in which the central tube described above is disposed almost in the center of a wholly or partially detachable shielding plate disposed at the upper end of the reaction tube. Usually disposed are an unreacted gas-feeding room at the upper part of the reaction tube in the reactor described above and a lower collecting room for reaction gas at the lower part of the reaction tube.

Further, the present invention provides a reactor for methanol synthesis, wherein plural reaction tubes are disposed in the inside thereof; an inner tube closed at a lower end thereof is disposed almost in the center of the reaction tube; a central tube is disposed almost in the center of the inner tube; a circular space surrounded by the reaction tube and the inner tube is constituted as a granular catalyst-charged part; a shielding plate in which at lest one of the whole and a part thereof is detachable is disposed at the upper end of said reaction tube; said central tube is connected almost to the center of the shielding plate; fed unreacted gas flows downwards from the upper part of the central tube to flow into the inner tube from the lower outlet of the central tube; and further, said unreacted gas flows upwards through a circular duct surrounded by the inner tube and the reaction tube and flows downwards from the upper part of the granular catalyst-charged part.

The production process of the present invention comprises a synthetic gas production step, a methanol synthesis step and a distillation step, and refined methanol is produced by passing in order through these steps.

The reactor used in the methanol synthesis step is provided with the inner tube closed at a lower end thereof disposed almost in the center of the reaction tube, and the central tube is disposed almost in the center of the inner tube to form a granular catalyst-charged layer in a circular space surrounded by the reaction tube and the inner tube. This allows unreacted gas which is synthetic gas to flow downwards through the upper part of the central tube from the unreacted gas-feeding room and flow into the inner tube from the lower exit of the central tube. Then, the unreacted gas flows upwards through a circular duct surrounded by the inner tube and the central tube, and subsequently it flows downwards from the upper part of the circular catalyst layer. Further, the foregoing central tube in which the unreacted feed gas flows is connected almost to the center of a wholly (entirely) or partially detachable shielding plate disposed at the upper end of the reaction tube described above.

In the reactor described above, the lower end of the inner tube with the lower end thereof closed disposed almost in the center of the reaction tube may be in an upper position than the lower end of the reaction tube.

Further, in the reactor described above, the lower end of the central tube disposed almost in the center of the inner tube is preferably in a position which is farther by $1/10$ to $2/3$ of the length of the reaction tube from the upper end of the reaction tube.

Use of the reactor described above leads to an improvement in the temperature distribution of the reaction tube in a longitudinal direction and a reduction in the peak temperature of the catalyst layer as compared with use of a conventional reactor for a synthetic step. Further, the temperature distribution of the reaction tube is made more uniform in the longitudinal direction of the catalyst tube, and the faster reaction rate than ever is obtained in the rear flow part thereof.

Thus, according to the production process of the present invention, use of the reactor described above makes it possible to suitably control heat generated in the methanol synthesis reaction without reducing the reaction rate. As a result thereof, ethanol and dimethyl ether which are products formed by side reaction can be inhibited from being formed. Accordingly, it becomes possible to reduce the amount of heat required for separating methanol in a separation and refining system in the distillation step subsequent to the synthesis step (synthetic system), and the separation and refining system can be reduced in a size.

BRIEF DESCRIPTION OF THE INVENTION

Figure 1:
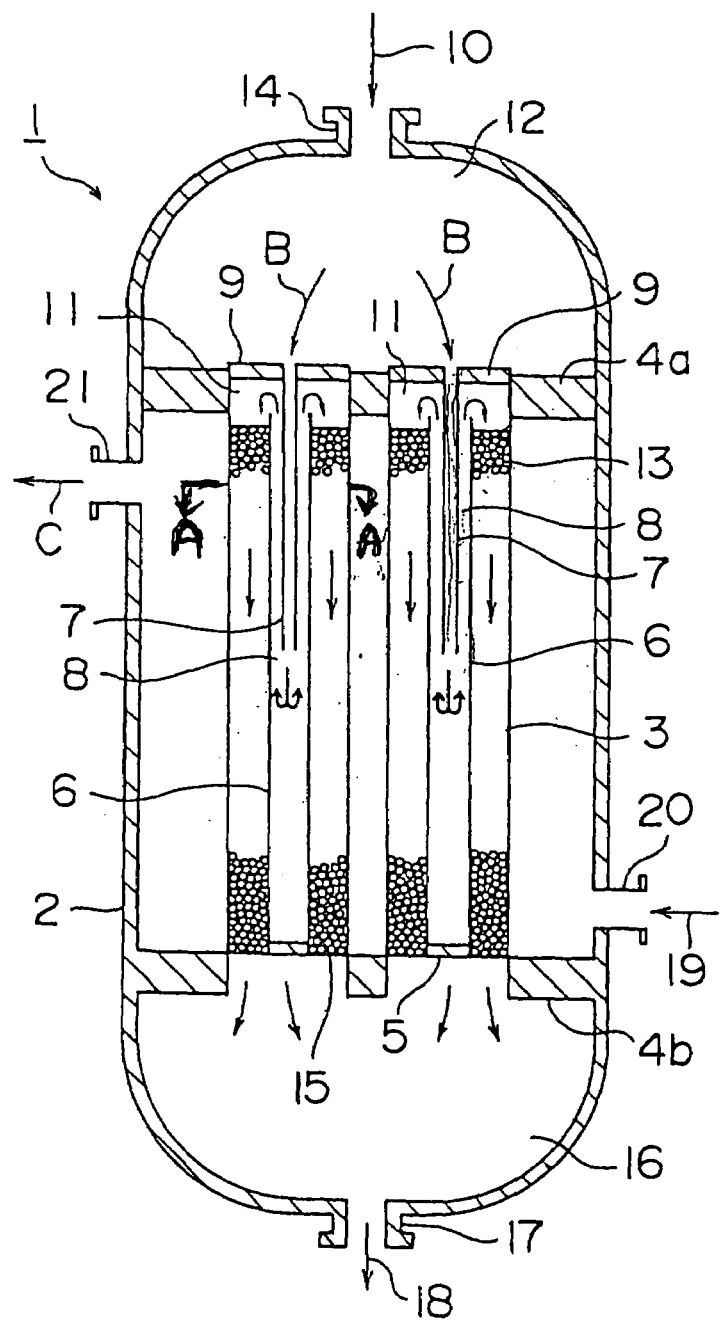
FIG. 1 is a cross section showing the constitution of the reactor used for the methanol synthesis step in the present invention.
Figure 1A:
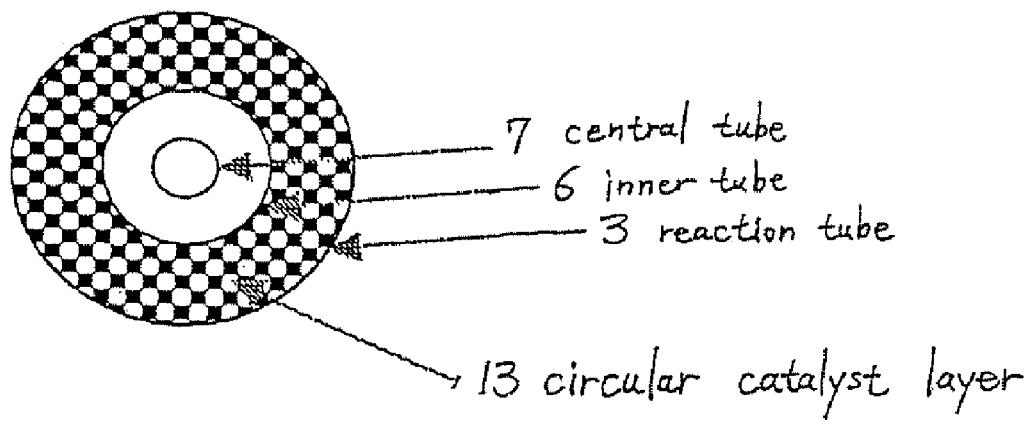
FIG. 1A is a cross-sectional view of FIG. 1 taken along the lines A—A.

The reference numerals shown in these figures are defined as follows: 1, Reactor; 2, Casing; 3, Reaction tube; 4a,4b, Tube plates; 5, Plug; 6, Inner tubes; 7, Central tube; 8, Circular duct; 9, Shielding plate; 10, Unreacted gas; 11, inlet of catalyst layer; 12, Unreacted gas-feeding room; 13, Circular catalyst layer; 14, Unreacted feed gas nozzle; 15, Outlet of catalyst layer; 16, Lower collecting room; 17, Outlet nozzle of reactor; 18, Resulting gas; 19, Boiling liquid; 20, Inlet nozzle; 21, Outlet nozzle; 22,23, Distillation columns; M, Synthetic gas (raw material gas); R, Recycle gas.

DETAILED DESCRIPTION OF PREFERRED EMBODIMENTS

The embodiment of the present invention shall be explained with reference to attached drawings.

The schematic structure of the reactor used in the methanol synthesis step in the embodiment of the present invention is shown in FIG. 1.

The methanol production process of the present invention comprises a synthetic gas production step in which hydrocarbon is reacted with steam to generate synthetic gas comprising main components of hydrogen, carbon monoxide and carbon dioxide, a methanol synthesis step in which the synthetic gas described above reacts on a methanol synthesis catalyst and resulting crude methanol is recovered in the form of liquid and a distillation step in which recovered crude methanol described above is distilled to be separated into waste water containing low boiling organic compounds and high boiling organic compounds and refined methanol, and the above process is carried out by passing in order through these steps.

In the methanol production process of the present invention, hydrocarbon such as methane first reacts with steam in the synthetic gas production step to generate synthetic gas comprising main components of hydrogen, carbon monoxide and carbon dioxide.

Then, in the methanol synthesis step using the reactor shown in FIG. 1, the synthetic gas described above reacts on a copper base methanol synthesis catalyst usually at a reaction pressure of 80 to 120 kg/cm$^2$·G, preferably 80 to 100 kg/cm$^2$·G, a catalyst layer inlet temperature of 180 to 260° C., preferably 200 to 240° C., a catalyst layer outlet temperature of 220 to 250° C., preferably 240 to 250° C., and a catalyst layer maximum temperature of 250 to 280° C., preferably 250 to 260° C., and resulting crude methanol is recovered in the form of liquid.

Further, in the distillation step, recovered liquid crude methanol has low contents of ethanol and dimethyl ether which are by-products as compared with those of conventional processes, and it is separated and refined by a lower heat amount to be separated into refined methanol and waste water containing low boiling organic compounds and high boiling organic compounds.

A reactor 1 used in the methanol synthesis step of the present invention shall be explained (refer to FIG. 1).

In the reactor 1, an inner tube 6 with the lower end thereof closed is disposed almost in the center of a reaction tube 3, and a central tube 7 is disposed almost in the center of the inner tube 6. A circular space surrounded by the reaction tube 3 and the inner tube 6 is a circular catalyst layer 13, and a granular catalyst used for carrying out methanol synthesis is charged therein. At least one reaction tube 3 can be disposed in the reactor 1, and it comprises preferably plural tubes as shown in FIG. 1. The lower end of the inner tube 6 with the lower end thereof closed can be in an upper position than the lower end of the reaction tube 3.

The catalyst charged into the circular catalyst layer 13 in the circular space surrounded by the reaction tube 3 and the inner tube 6 shall not specifically be restricted, and any catalysts can widely be used as long as they have a catalytic ability for methanol synthesis. Specific examples thereof include copper base catalysts. The form of these catalysts shall never be restricted as well, and granular catalysts are usually used.

Further, the central tube 7 disposed almost in the center of the inner tube 6 is installed almost in the center of a wholly or partially detachable shielding plate 9 disposed at the upper end of the reaction tube. The lower end of this central tube 7 is preferably in a position which is farther by 1/10 to 2/3 of the length of the reaction tube from the upper end of the reaction tube.

Provided are an unreacted gas-feeding room 12 at the upper part of the reaction tube 3 in the reactor 1 and a lower collecting room 16 for reaction gas at the lower part of the reaction tube 3.

In such reactor 1, unreacted gas 10 produced in the synthetic gas production step of the present invention is introduced into the reactor 1 from a feed gas nozzle 14 at the upper part of the reactor. The unreacted gas flows downwards from the upper part of the central tube 7 through the inlet B at the central tube 7 partitioned by a shielding plate 9 from the unreacted gas-feeding room 12 to flow into the inner tube 6 from the lower outlet of the central tube 7.

Then, the unreacted gas flows upwards through a circular duct 8 surrounded by the inner tube 6 and the central tube 7 to reach the upper end of the circular catalyst layer 13. When the unreacted gas flows downwards through the circular catalyst layer 13 surrounded by the reaction tube 3 and the inner tube 6, the synthesis reaction of methanol goes on to generate heat in the tube.

Resulting gas 18 produced by this methanol synthesis reaction is stored in a lower collecting room 16 through the outlet 15 of the catalyst layer and then flows out from the outlet nozzle 17 of the reactor. This resulting gas 18 is sent to a separation system or a refining system in which a subsequent distillation step is carried out.

Figure 2:
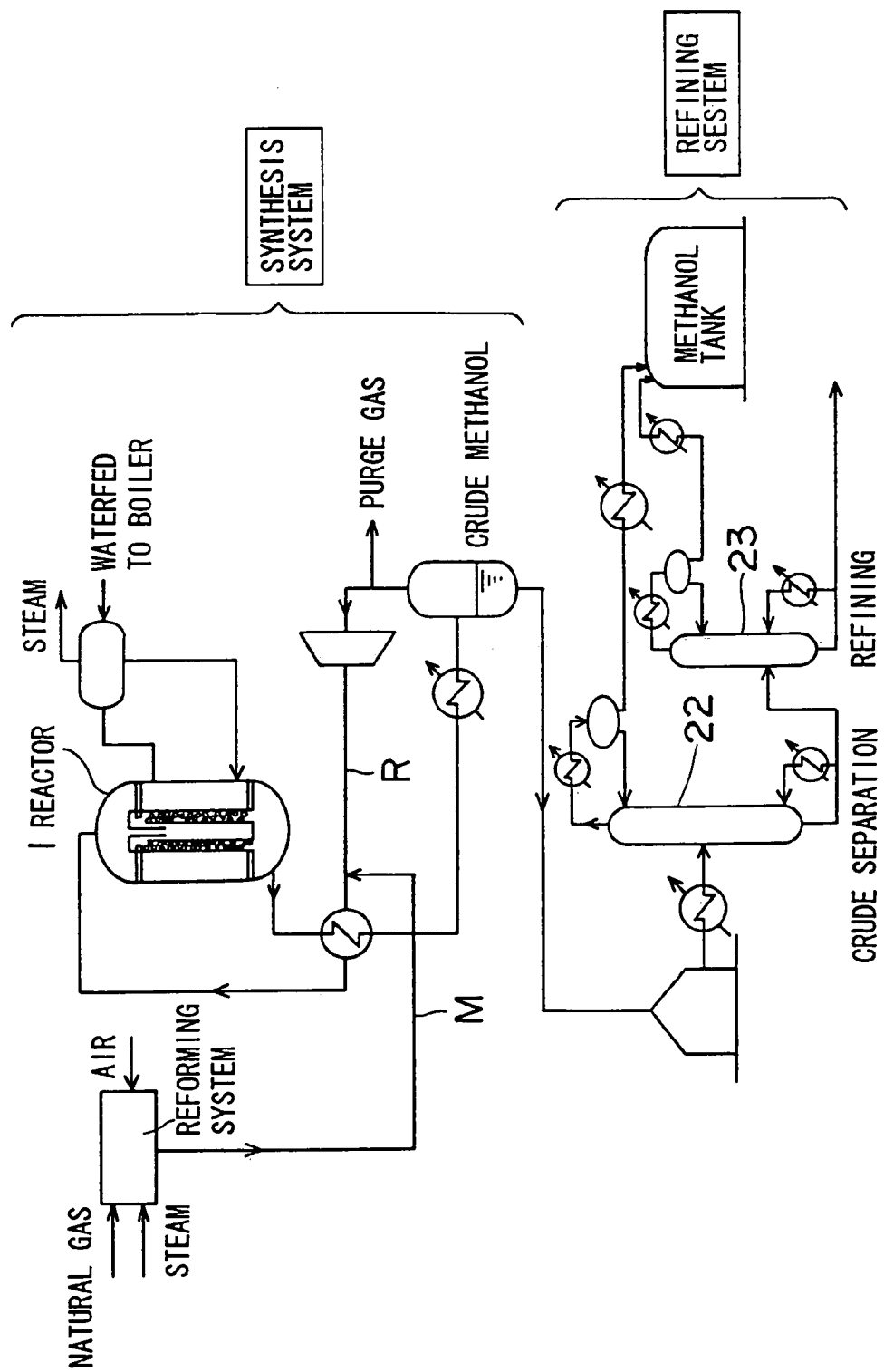
FIG. 2 is a drawing showing the process flow of the methanol production plant according to the present invention.

One example of the process flow of a methanol production plant having the reactor described above in the methanol synthesis step is shown in FIG. 2. This methanol production plant comprises a refining system in which a step for producing synthetic gas from natural gas is carried out, a synthesis system in which a methanol synthesis step using the reactor 1 described above is carried out and a refining system in which a distillation step for separating and refining methanol is carried out.

One example showing the specific constitution of the synthesis system described above comprises the reactor 1 (methanol synthesis column) described above, a heat exchanger for resulting gas and recycle gas (R) and a boiler water-circulating apparatus for recovering reaction heat.

One example showing the specific constitution of the subsequent refining system described above comprises a distillation column 22 for roughly separating crude methanol into refined methanol and components other than methanol and a distillation column 23 for separating trace amounts of components such as ethanol to carry out refining. Separated, refined methanol is stored in a methanol tank.

Figure 3A:
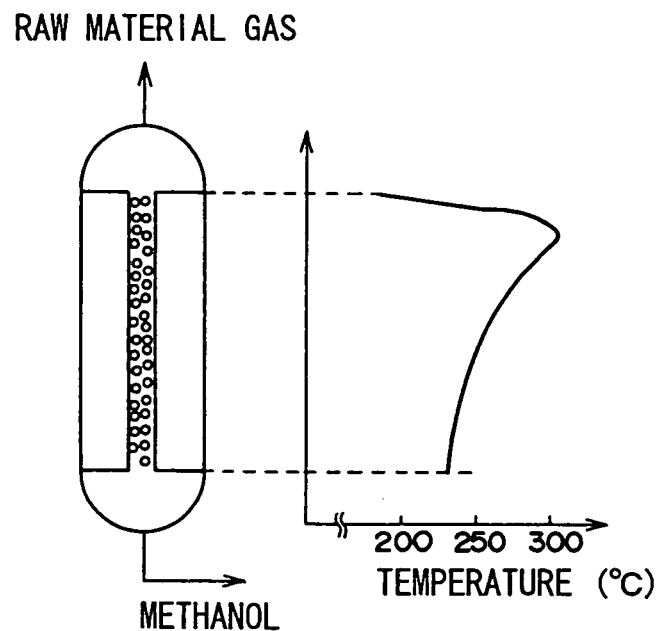
FIG. 3 is a drawing showing the temperature distribution of the catalyst layer in the reactor.
Figure 3B:
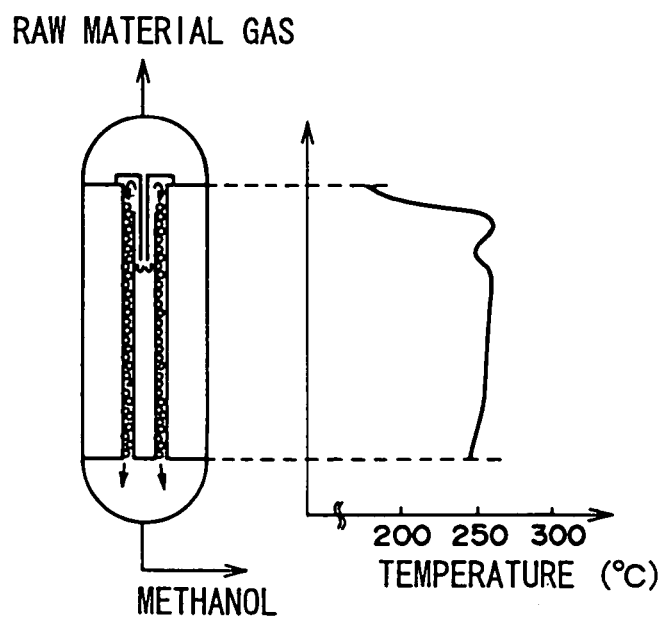

There are shown respectively in FIG. 3(a), the temperature distribution of a catalyst layer in the reactor observed when a conventional reactor (tubular type reactor) is used in a methanol synthesis step and in FIG. 3(b), the temperature distribution of the catalyst layer in the reactor observed when the reactor shown in FIG. 1 is used.

In general, it is known that the higher the temperature, the faster the reaction rate is, but at the same time the more the side reactions are liable to take place. Accordingly, it is ideal in the methanol synthesis step that the temperature distribution corresponding to the maximum level of the reaction rate is achieved at a temperature level at which side reactions do not occur. Further, in order to reduce the amount of heat required in the subsequent refining system, it is necessary to optimally control the temperature while synthesizing methanol in the synthesis system comprising the reactor of FIG. 1 so that by-products such as ethanol are controlled to small amounts.

In the present invention, use of the specific rector described above makes it possible, as shown in FIG. 3, to allow the synthetic reaction to proceed with a lower peak temperature in the catalyst layer and with a more uniform temperature distribution there in the longitudinal direction.

According to the production process of the present invention, the side reactions in the synthetic system can be controlled, and ethanol and dimethyl ether which are by-products can be inhibited from being formed, so that it becomes possible to reduce the amount of heat required for separating methanol in the separation and refining system subsequent to the synthetic system and make the apparatus small.

In addition, according to the present invention, the temperature distribution in the longitudinal direction of the reaction tube in the reactor can be made uniform in the methanol synthesis step, and the reaction rate at the rear flow part of the reaction tube can be enhanced, so that the higher methanol formation rate than ever can be achieved.

Further, in the present invention, use of the reactor having the specific structure makes it possible to feed a raw material gas of a low temperature to a part having the peak temperature in a catalyst layer at the upper part of a reaction tube in a conventional reactor, and the peak temperature of the catalyst layer can be effectively reduced, so that the temperature distribution in the longitudinal direction of the reaction tube in the reactor is made uniform, and the deterioration rate of the catalyst is slowed down. This makes it possible to operate the reactor of the present invention over a longer period of time than that of the conventional reactor and operate the whole methanol production process over a long period of time.

The present invention shall be explained below with reference to examples, but the present invention shall by no means be restricted by these examples.

EXAMPLE 1

A methanol production plant constituted from a reforming system, a synthesis system and a refining system as shown in FIG. 2 was used to carry out the production of methanol via a synthetic gas production step, a methanol synthesis step and a distillation step. The reactor 1 shown in FIG. 1 was used in the synthetic system, and a conventional tubular type reactor was used as well for the sake of comparison.

The concentrations of impurities in gases containing methanol which flow out from the reactors in the methanol synthesis system were compared to find that as shown in the following Table 1, the amounts of ethanol and dimethyl ether formed in the reactor of the present invention were reduced as compared with those of the conventional tubular type reactor.

TABLE 1

|  | Inventive reactor | Tubular type |
|---|---|---|
| Ethanol | 0.5 | 1 |
| Dimethyl ether | 0.7 | 1 |

Shown in above Table 1 is relative comparison in which the value obtained by using the tubular type reactor was set at 1.

Further, compared were the heating amounts in the refining system subsequent to the synthesis system using the reactors described above in the methanol production plant shown in FIG. 2.

TABLE 2

|  | Inventive reactor-applied process | Tubular type-applied process |
|---|---|---|
| Heating amount ratio | 0.9 | 1 |

As shown in the Table 2 described above, in the methanol production process of the present invention to which the reactor shown in FIG. 1 was applied, the heating amount could be reduced by about 10% in the refining system as compared with that of the production process using the conventional tubular type reactor.

Thus, the temperature distribution in the longitudinal direction of the reaction tube was improved as shown in FIG. 3 by using the reactor described above, so that the peak temperature of the catalyst layer was reduced.

Further, the temperature distribution became more uniform in the longitudinal direction of the catalyst tube, and the higher reaction rate than ever was obtained at the rear flow part. That is, the reactor described above is characterized by that it can appropriately control heat generated in the methanol synthesis reaction without reducing the reaction rate.

As a result thereof, ethanol and dimethyl ether which are products formed by side reactions can be inhibited from being formed in the methanol synthesis step, and it becomes possible to reduce a heat amount required for separating methanol in the separation and refining system subsequent to the synthetic system, so that the separation and refining system can be small-sized.

What is claimed is:

1. A reactor for methanol synthesis comprising a reactor casing having an inlet end and an outlet end with the reactor casing having a plurality of reaction tubes of substantially equal length and of substantially equal diameter with upper and lower ends disposed on the inside thereof in a coaxial symmetrical arrangement spaced apart from the reactor casing and being in communication with an upper chamber into which unreacted gas is fed into said casing through said inlet end; each reaction tube having an inner tube disposed almost in the center of the reaction tube to form a first passageway of circular cross section between the inner tube and the surrounding reaction tube with the inner tube being closed at a lower end thereof facing a lower chamber located symmetrically opposite said upper chamber and being open at the upper end to said first passageway, said reactor having a single charge of granular catalyst with said charge being stored in said first passageway to form a catalyst charged part therein surrounded by said one or more reaction tubes; a central tube disposed almost in the center of the reactor with the central tube extending downwardly from said upper chamber a fixed distance above the lower end of said reaction tube for forming a second passageway of circular cross section between said central tube and an inner tube; an upper shielding plate for partitioning the upper end of said reaction tubes from said upper chamber, tube plates separating the reaction tubes from said reactor casing with said upper and lower chambers each defining a confined space of predetermined volume at symmetrically opposite ends of said reactor to facilitate a smooth flow of gas therethrough, wherein said unreacted gas flows downwards from said upper chamber through the upper part of the central tube flowing from said second passageway through said catalyst in said first passageway from the upper end of said first passageway and discharges from an outlet located in said lower end and wherein the length of said central tube is between 1/10 to 2/3 of the length of a reaction tube measured from the upper end of the reaction tube.

2. The reactor for methanol synthesis as described in claim 1, wherein each inner tube is disposed almost vertically in said reactor.

* * * * *